US012575906B2

(12) United States Patent　　　　(10) Patent No.:　US 12,575,906 B2

Avshalom　　　　　　　　　　　　　(45) Date of Patent:　Mar. 17, 2026

(54) APPARATUS FOR PUTTING A GLOVE ON A PALM HAND

(71) Applicant: Jacob Maklouf CHOCRON, Dubai (AE)

(72) Inventor: Shlomo Matan Shalom Avshalom, Beit Shemesh (IL)

( * ) Notice: Subject to any disclaimer, the term of this patent is extended or adjusted under 35 U.S.C. 154(b) by 0 days.

(21) Appl. No.: 19/122,738

(22) PCT Filed: Nov. 4, 2022

(86) PCT No.: PCT/IL2022/051166

§ 371 (c)(1),
(2) Date: Apr. 20, 2025

(87) PCT Pub. No.: WO2024/095249

PCT Pub. Date: May 10, 2024

(65) Prior Publication Data

US 2026/0007485 A1　　Jan. 8, 2026

(51) Int. Cl.
A61B 42/50　　　　(2016.01)
A61B 42/40　　　　(2016.01)

(52) U.S. Cl.
CPC .............. A61B 42/50 (2016.02); A61B 42/40 (2016.02)

(58) Field of Classification Search
CPC ........ A47G 25/904; A61B 42/40; A61B 42/50
See application file for complete search history.

(56) References Cited

U.S. PATENT DOCUMENTS

| 429,890 | A | * | 6/1890 | Crispell ................. A47G 25/92 |
| | | | | 223/111 |
| 4,909,413 | A | * | 3/1990 | McCutcheon ....... A47G 25/904 |
| | | | | 221/25 |
| 5,878,909 | A | * | 3/1999 | Rogow .................. A61B 42/50 |
| | | | | 221/45 |

(Continued)

FOREIGN PATENT DOCUMENTS

| FR | 2962314 A1 | * | 1/2012 | ............. A61B 42/40 |
| JP | 2021020030 A | | 2/2021 | |
| WO | WO-2021152570 A1 | * | 8/2021 | ............. A61B 42/50 |

OTHER PUBLICATIONS

Written Opinion for PCT Application No. PCT/IL2022/051166 mailed Mar. 8, 2023, 5 pages (Year: 2023).*

*Primary Examiner* — F Griffin Hall

(57) ABSTRACT

A gloving apparatus that has a glove-opening device and a glove-lifting-and-positioning device. The glove-lifting-and-positioning device includes a linear actuator with a moveable rod that is ended with a plurality of inserting teeth, a rotating actuator that is designed to rotate the glove-lifting-and-positioning device, and a lifting arm with a lifting actuator that are designed to lift up and lower down the glove-lifting-and-positioning device. The glove-lifting-and-positioning device is designed to insert the plurality of the inserting teeth into a corresponding plurality of matching holes at a glove holder to which a glove is attached and to insert the opening of the glove over grasping pins of the glove-opening device. The glove-opening device can stretch open the glove opening and when an air pump creates sub-pressure then the glove expands to a size suitable for a hand to be inserted.

3 Claims, 40 Drawing Sheets

(56)     References Cited

U.S. PATENT DOCUMENTS

| | | | | |
|---|---|---|---|---|
| 6,375,034 B1 * | 4/2002 | Corbett | ................. | A61B 42/50 |
| | | | | 221/45 |
| 6,932,253 B2 * | 8/2005 | Sato | ..................... | A47G 25/904 |
| | | | | 223/111 |
| 7,635,067 B1 * | 12/2009 | Flynn | ..................... | A61B 42/40 |
| | | | | 223/111 |
| 7,712,642 B2 * | 5/2010 | Gaines | ................... | A61B 42/40 |
| | | | | 223/111 |
| 10,143,528 B2 * | 12/2018 | Gaines | ................. | A47G 25/904 |
| 10,349,769 B2 * | 7/2019 | Avshalom | ............ | A47G 25/904 |
| 10,512,516 B1 * | 12/2019 | Rogers | .............. | A41D 19/0093 |
| 10,517,691 B2 * | 12/2019 | Ahrens | ................. | A61B 50/15 |
| 10,610,319 B2 * | 4/2020 | Backhaus | ............ | A47G 25/904 |
| 11,617,629 B2 * | 4/2023 | Shalom Avshalom | ........................ | |
| | | | | A61B 42/50 |
| | | | | 223/111 |
| 11,779,143 B2 * | 10/2023 | Howard | ................. | A47G 25/80 |
| | | | | 223/111 |
| 2004/0149788 A1 | 8/2004 | Kaisha | | |
| 2021/0228299 A1 * | 7/2021 | Löfholm | ............... | A61B 42/50 |
| 2022/0202221 A1 * | 6/2022 | Shafran | .................. | A61B 42/50 |

* cited by examiner

100

103

104

APPARATUS FOR PUTTING A GLOVE ON A PALM HAND

TECHNICAL FIELD

The present invention refers to a gloving apparatus for putting a sterile glove on a palm hand.

BACKGROUND ART

The inventor of the invention of the present disclosure is also the inventor of the invention subject matter of PCT/IL2020/051334 in which stated that it is customary and sometimes necessary to use sterile gloves in operating theaters to perform medical surgeries, laboratories, and in various other places in which a sterile environment must be maintained. The user, for instance a surgeon preparing for surgery, usually scrubs and disinfects his or her hands with soap and a disinfectant and then puts on a pair of sterile gloves. While putting the gloves on his or her hands, the user touches the gloves, potentially contaminating the exterior of the glove. Touching the exterior of the gloves, even after scrubbing and disinfecting, may contaminate them with bacteria. The present invention describes the apparatus for putting gloves that is disclosed in PCT/IL2020/051334 with some innovative improvements.

LIST OF DRAWINGS

The intention of the drawings attached to the application is not to limit the scope of the invention and its application. The drawings are intended only to illustrate the invention and they constitute only one of its many possible implementations.

FIG. 1 presents a glove (100) with its opening (103) and the circumferential part (104) of the opening (103).

THE INVENTION

Figure 1:
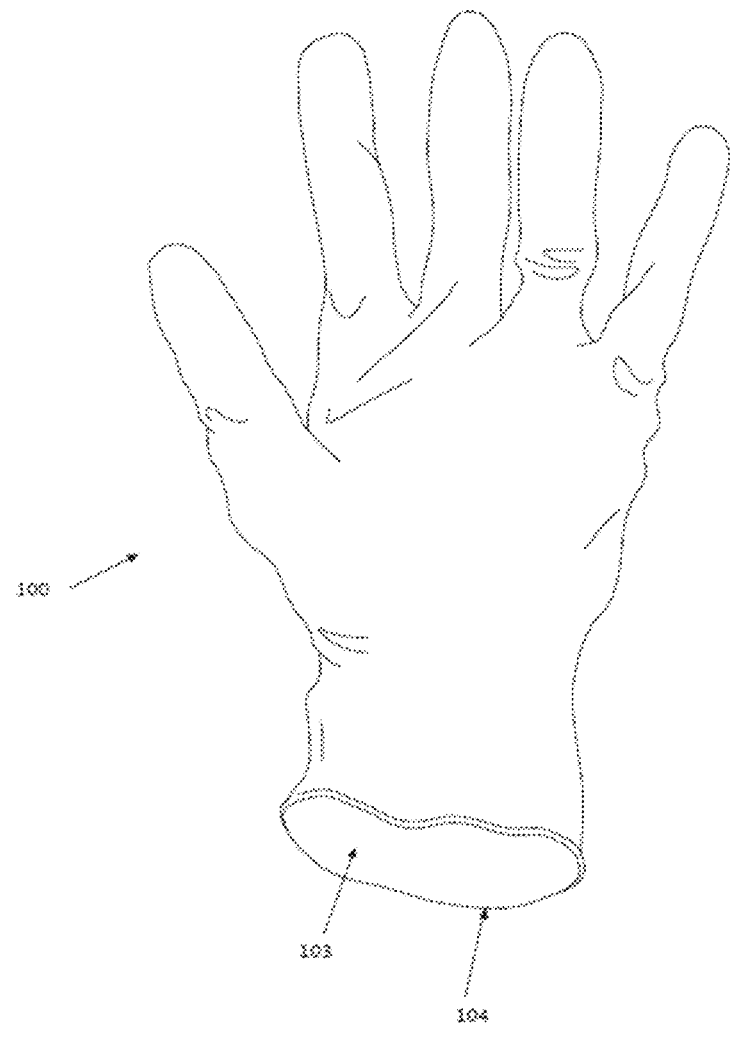

The main objective of the invention of PCT/IL2020/051334 is to provide a gloving apparatus (1) that is designed to help users to put gloves on their hands. The gloving apparatus (1) comprises a casing (2), a glove-opening device (3), a glove-lifting-and-positioning device (4), and an air pump (5).

The gloving apparatus (1) may contain a replaceable glove cartridge (7) that is designed to contain gloves (100). The gloves may be placed in the replaceable glove cartridge, one on top of the other. The replaceable glove cartridge may be a fixed as permanent part of the gloving apparatus that is refilled whenever the gloves run out, or alternatively, the entire replaceable cartridge may be replaced with a new replaceable glove cartridge, thus serving as a kind of disposable glove cartridge. In cases in which the sterility of the gloves must be maintained, the disposable, replaceable glove cartridge setup is more appropriate and recommended.

The glove-lifting-and-positioning device (4) is designed to lift a glove, possible from a replaceable glove cartridge, one glove at a time, and to position the glove opening (103) over the glove-opening device (3).

The gloving apparatus (1), as depicted in the drawings and as explained above, includes the casing (2), the glove-lifting-and-positioning device (4), the glove-opening device (3), and the air pump (5). The casing (2) is partially depicted in the drawings and it contains the above-mentioned parts of the gloving apparatus (1). The casing (2) may also contain the replaceable glove cartridge (7).

The glove-lifting-and-positioning device (4) includes:

(a) A base (43) with a linear actuator (41) that is equipped with a movable rod (411). When operating the linear actuator the movable rod is designed to move forth and back.

(b) A rotating actuator (44) that is designed to rotate the glove-lifting-and-positioning device (4). By operating the rotating actuator it is possible to rotate the glove-lifting-and-positioning device and to change the direction to which the movable rod is facing.

(c) A lifting arm (45) with a lifting actuator (46) that is designed to lift up and lower down the glove-lifting-and-positioning device (4). The drawings depict for example two lifting arms. By controlling the lifting actuator the position of the glove-lifting-and-positioning device is changed.

(d) The base also includes releasing rods (47). The movable rod (411) is ended with an inserting pin (42) and the movable rod (411) includes an adjustment piece (48) with adjustment rods (49).

The glove-lifting-and-positioning device (4) is designed to descend and reaches a glove holder (6) to which a glove (100) is attached and then to "pick up" the glove by the movable rod (411) due to the fact that the inserting pin (42) penetrated into a matching hole (61) in the glove holder (6) and locked it to the movable rod. At this stage the glove-lifting-and-positioning device (4) lifts the glove upward and forwards and presents the glove to the glove-opening device.

Some explanations about the gloves: The gloving apparatus (1) may include the replaceable glove cartridge (7) that includes several gloves (100). Each glove (100) is attached to a glove holder (6). The glove holder may be made of a flexible plastic that include several holding rods (62) that each of them is ended with a holding clip (63) to which the circumferential part (104) of the opening (103) of the glove (100) is attached and a matching hole (61) that match to the inserting pin (42) of the glove-lifting-and-positioning device (4). In this way, the inserting pin (42) is inserted into the matching hole (61), lock the glove holder (6) to it and take the glove holder with the glove to the glove-opening device (3). In order to center the inserting pin (42) directly to the matching hole (61) the movable rod (411) includes the adjustment piece (48) with the adjustment rods (49) that centering the inserting pin (42) straight to the matching hole (61) by embracing and surrounding the glove holder (6).

When the opening of the glove is inserted over the grasping pins (36) while they are in a closed position and these grasping pins (36) move to an open position then the glove is disconnected from the glove holder (6). At this stage, the glove-lifting-and-positioning device (4) is move back to bring another glove on demand. The glove-lifting-and-positioning device (4) get rid from the glove holder (6), which is now without a glove, by pulling back the movable rod (411) so that the glove holder (6) clashes with the releasing rods (47) that are connected to the base (43) causing the glove holder (6) to exit the inserting pin (42) and to fall down preferably to a trash can.

The drawings illustrate the glove-opening device (3) with a six-sided frame, although the invention may be implemented with a frame with more or less sides. The outer end (33) of each spreading rod (32) is attached to the polygonal circumferential frame (31) via an axial joint (34). The inner end (35) of each spreading rod (32) is equipped with a grasping pin (36). The glove-opening device (3) also includes a mechanism that changes the joint angle between the spreading rods (32) and the polygonal circumferential frame (31). The gloving apparatus (1) may include an adjuster (8) that covers the hole inside the polygonal circumferential frame (31) and that is designed to be closed when the apparatus (1) is not in used, and vice versa.

Method of operation of the gloving apparatus (1): The glove-lifting-and-positioning device (4) descends and picks up a glove (100) as described above. The glove-lifting-and-positioning device (4) then brings the opening of the glove over the grasping pins (36). Then the glove-opening device (3) goes from closed to open position, in other words, to a position in which the glove opening is stretched into the shape of the polygonal circumferential frame, and the glove, in fact, is sealing the opening of the glove-opening device. The air pump (5) then creates sub-pressure within the casing (2), causing the glove to inflate. The user can now insert his or her hand into the inflated glove which, as a result of its slight inward motion, is released from the grasping pins, remaining on the user's hand. A sensor that identifies full insertion of the hand into the glove or a pressing or touching switch may control the release of the glove from the grasping pins. In addition, the gloving apparatus is equipped with several activators that activate each of the above mentioned apparatus parts, as well as sensors that enable it to operate automatically.

Figure 2:
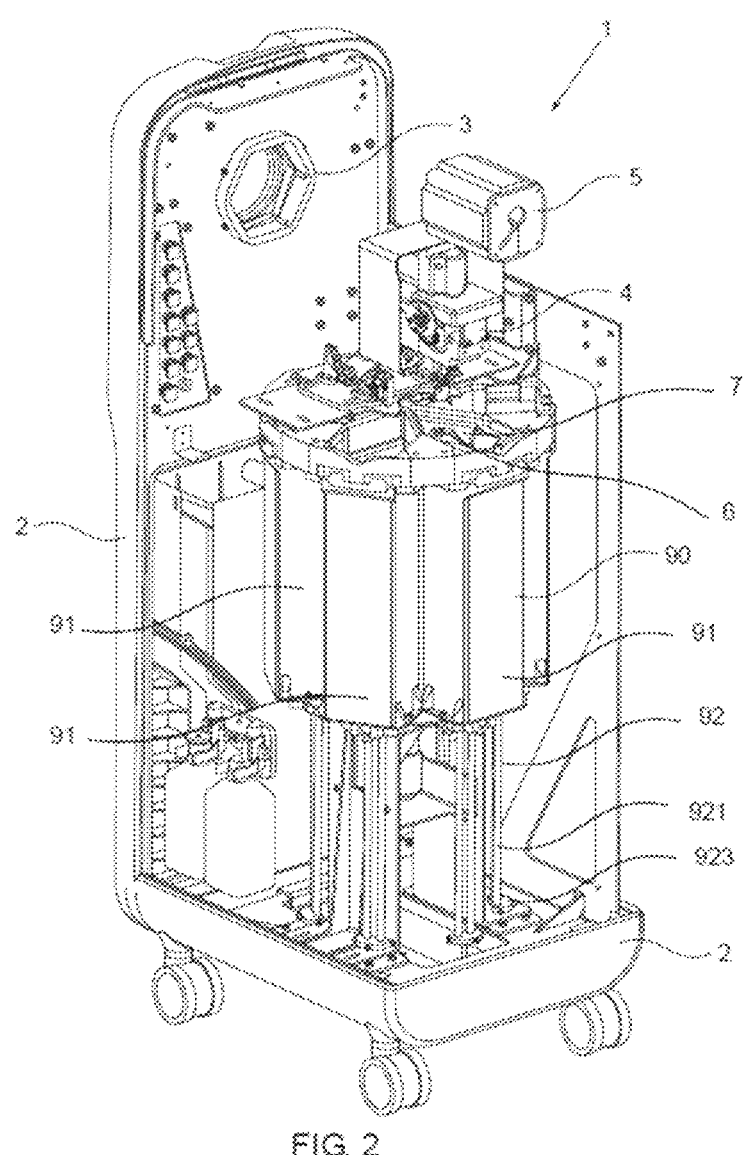
FIGS. 2 and 3 depict the gloving apparatus (1) that includes the casing (2), the glove-opening device (3), the glove-lifting-and-positioning device (4), the air pump (5) and the replaceable glove cartridge (7).
Figure 3:
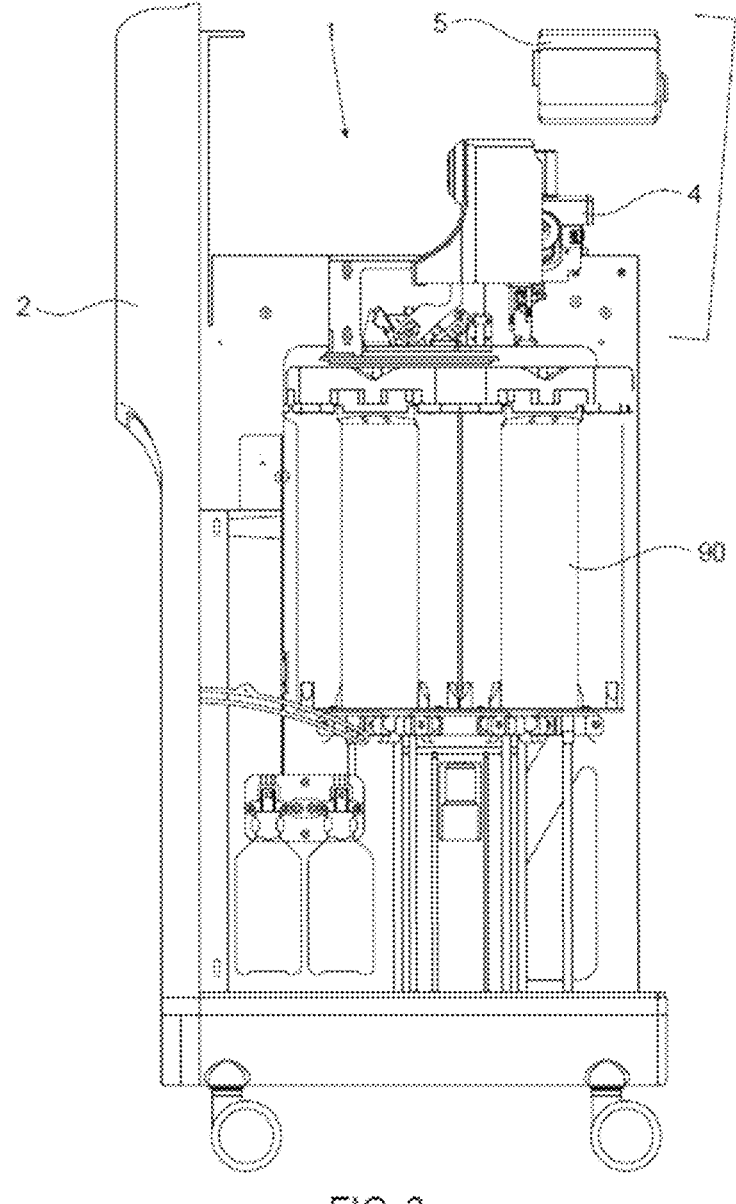
Figure 4:
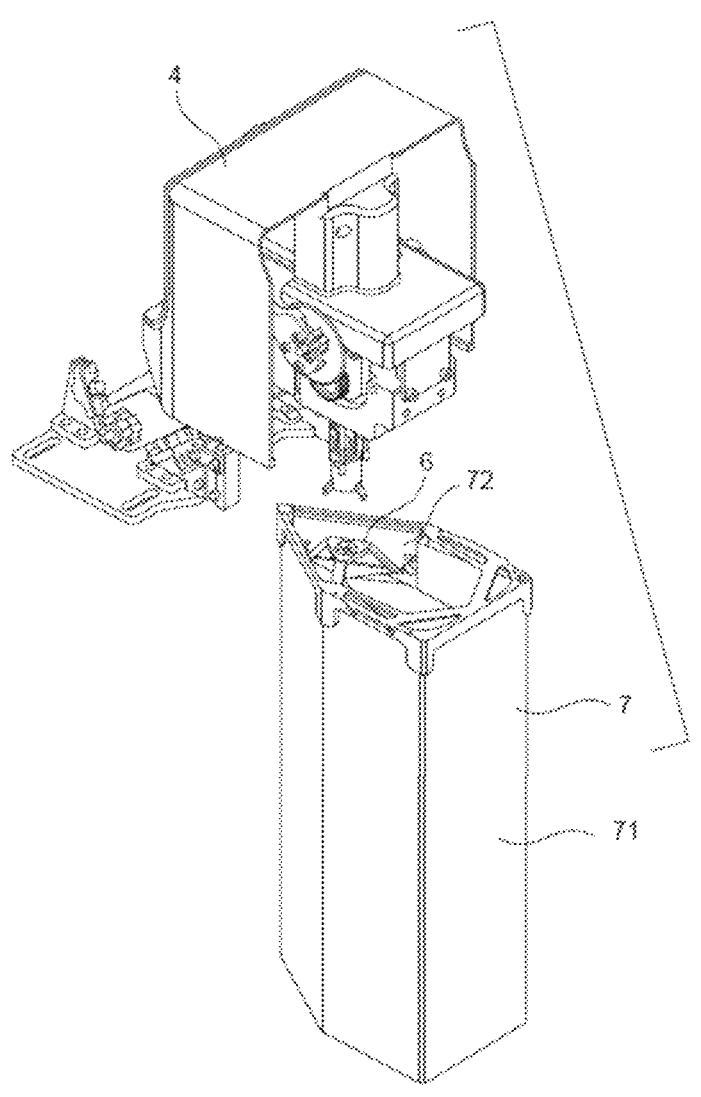
FIGS. 4 and 5 depict the glove-lifting-and-positioning device (4) when the movable rod (411) is facing downwards on the way to collect a glove from the replaceable cartridge (7).
Figure 5:
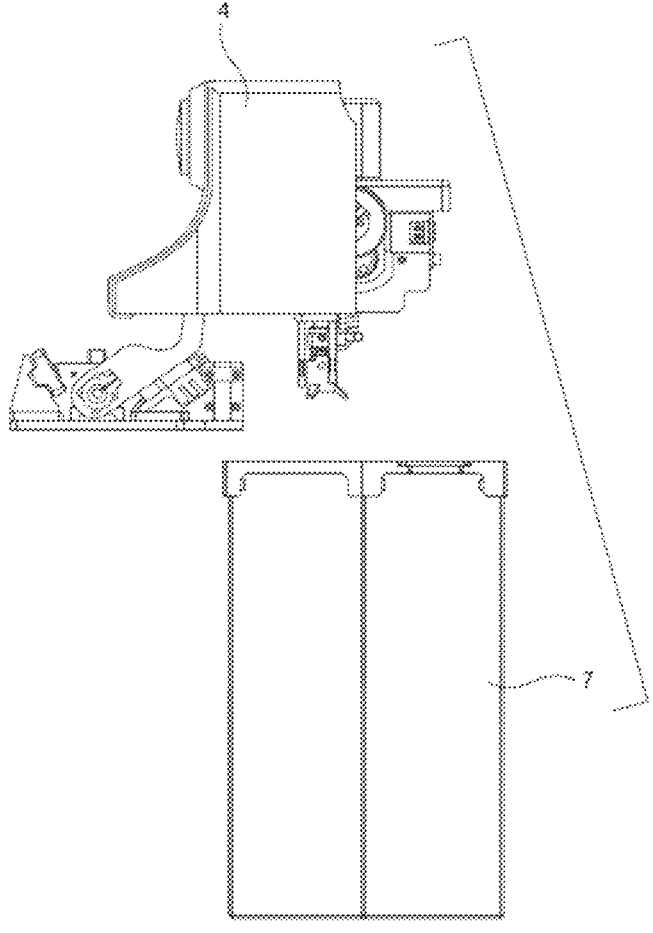
Figure 6:
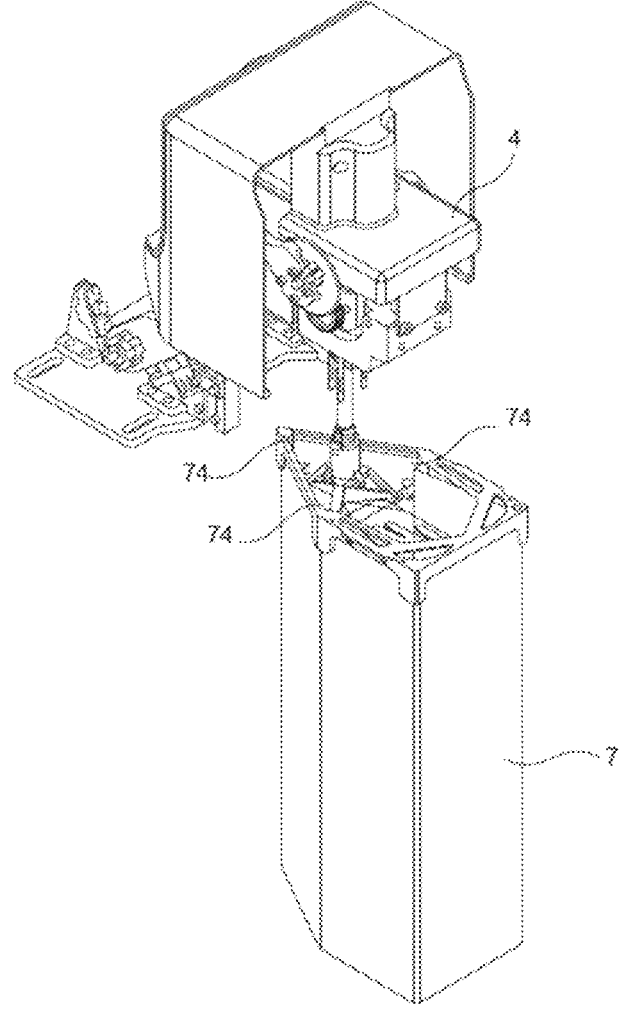
FIGS. 6 and 7 depict the glove-lifting-and-positioning device (4) when the inserting pin is inserted in the matching hole of the glove holder.
Figure 7:
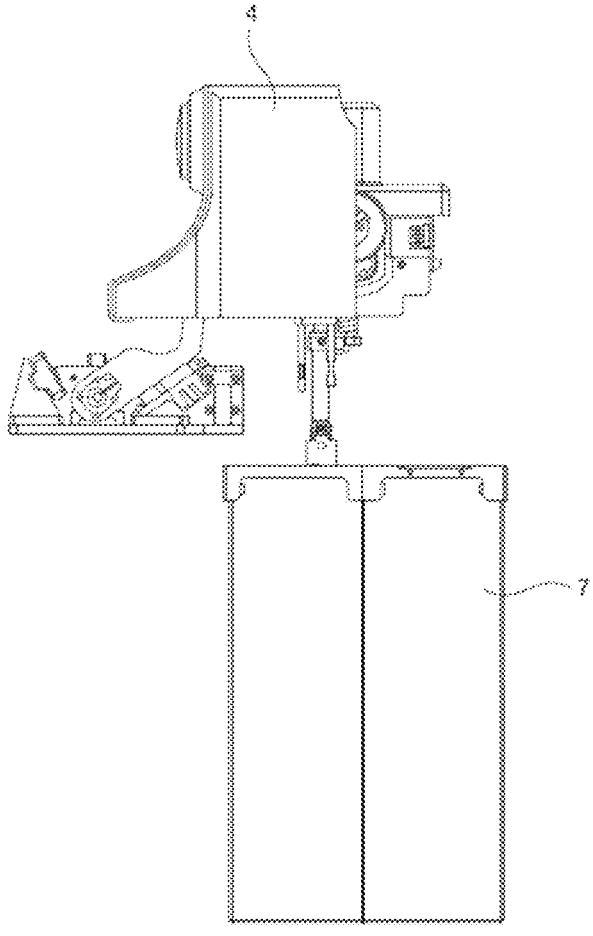
Figure 8:
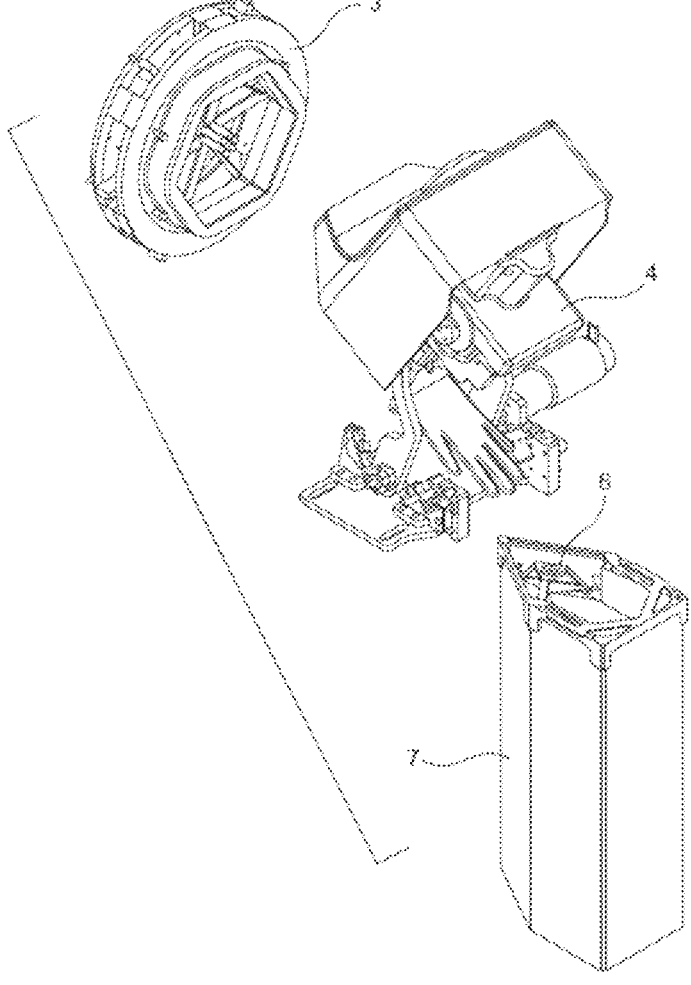
FIGS. 8 and 9 depict the glove-lifting-and-positioning device (4) in diagonal state and that holds a glove on the way to wear the glove on the glove-opening device (3).
Figure 9:
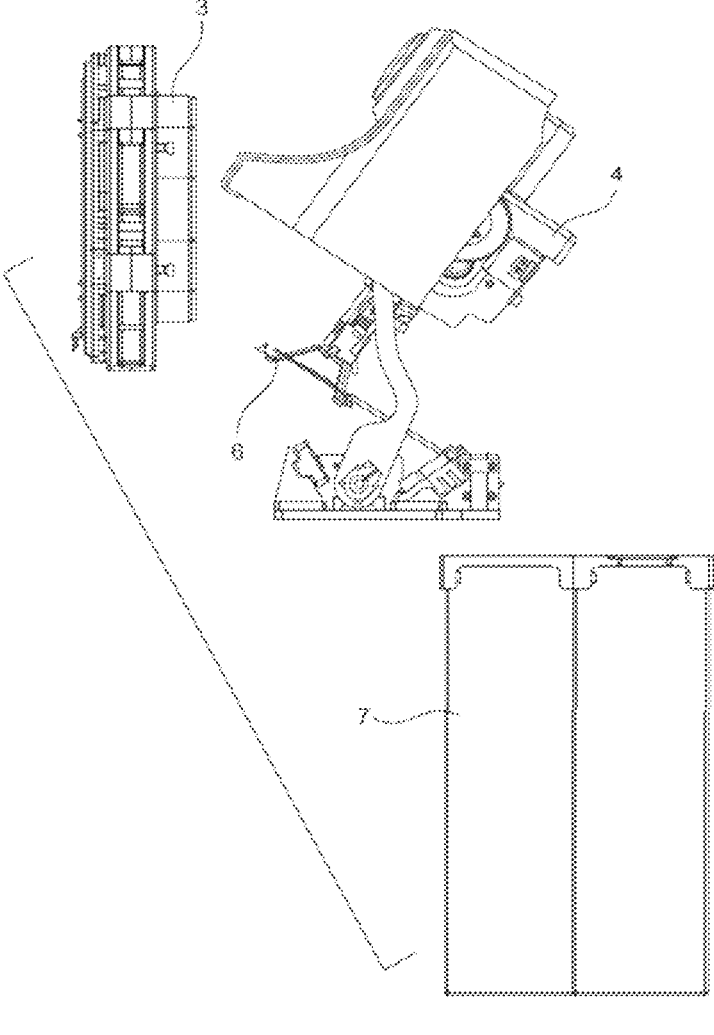
Figure 10:
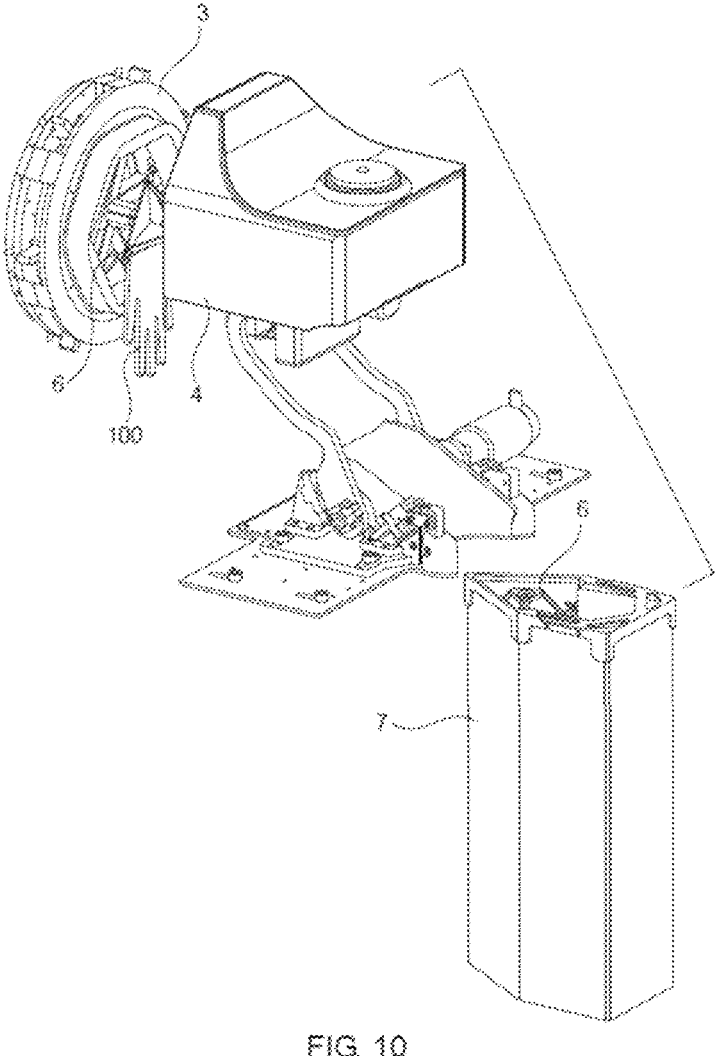
FIGS. 10 and 11 depict the glove-lifting-and-positioning device (4) in horizontal state and that holds a glove and wears the glove on the glove-opening device (3).
Figure 11:
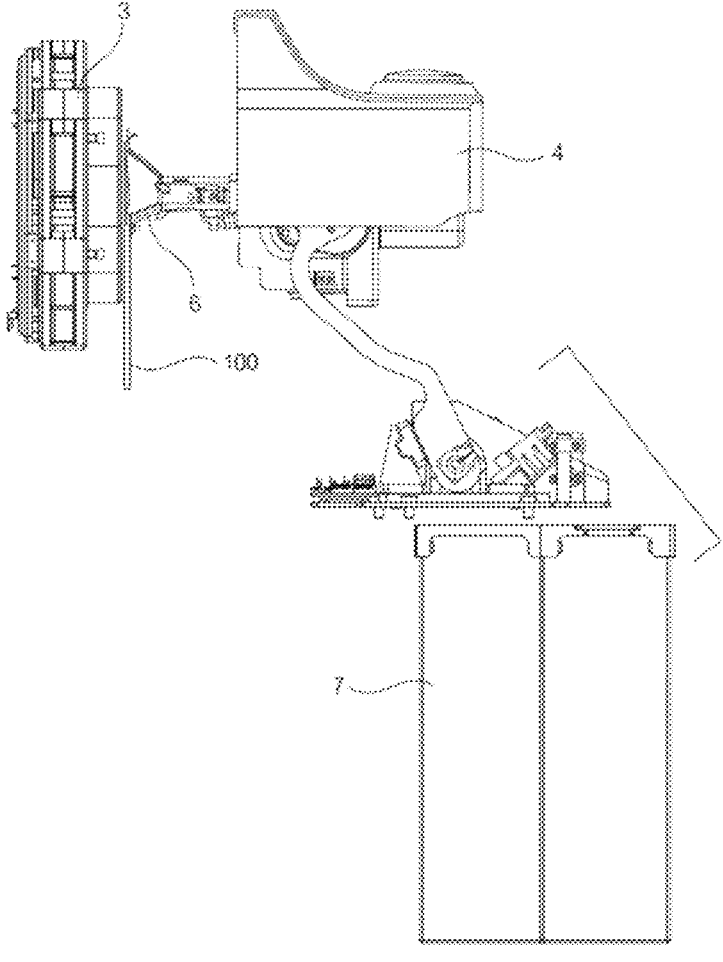
Figure 12:
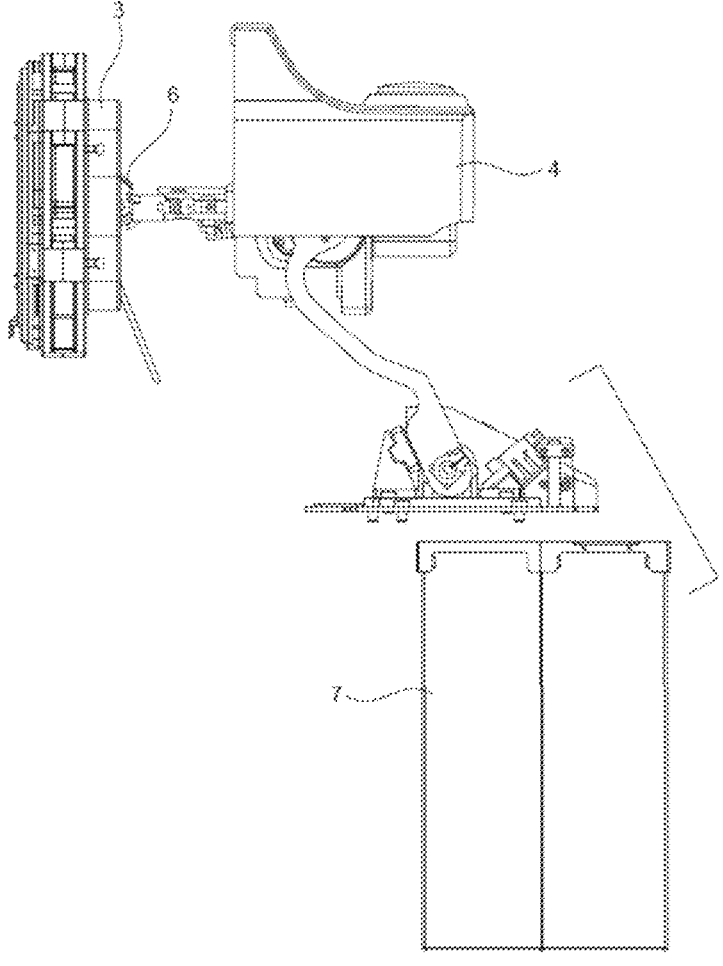
FIGS. 12 and 13 depict the glove-lifting-and-positioning device (4) that wears the glove on the glove-opening device (3).
Figure 13:
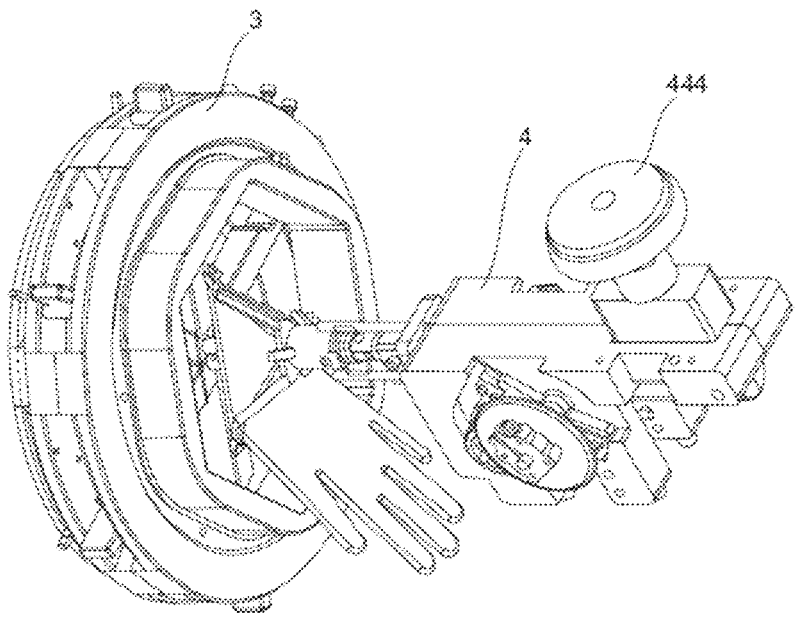

FIG. 1 presents a glove (100) with its opening (103) and the circumferential part (104) of the opening (103). FIGS. 2 and 3 depict the gloving apparatus (1) that includes the casing (2), the glove-opening device (3), the glove-lifting-and-positioning device (4), the air pump (5) and the replaceable glove cartridge (7). FIGS. 4 and 5 depict the glove-lifting-and-positioning device (4) when the movable rod (411) is facing downwards on the way to collect a glove from the replaceable cartridge (7). FIGS. 6 and 7 depict the glove-lifting-and-positioning device (4) when the inserting pin is inserted in the matching hole of the glove holder. FIGS. 8 and 9 depict the glove-lifting-and-positioning device (4) in diagonal state and that holds a glove on the way to wear the glove on the glove-opening device (3). FIGS. 10 and 11 depict the glove-lifting-and-positioning device (4) in horizontal state and that holds a glove and wears the glove on the glove-opening device (3). FIGS. 12 and 13 depict the glove-lifting-and-positioning device (4) that wears the glove on the glove-opening device (3).

Figure 14:
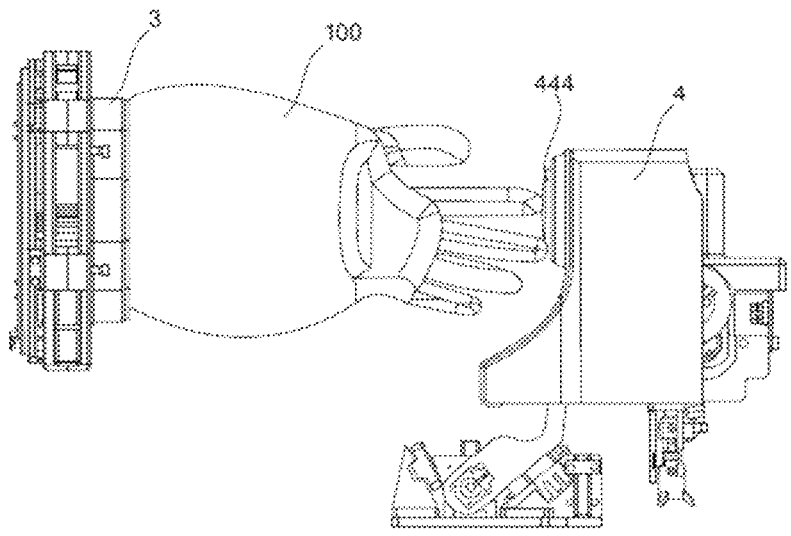
FIG. 14 depicts the glove (100) when inserted on the grasping pins and inflated and ready to receive the user's hand.
Figure 15:
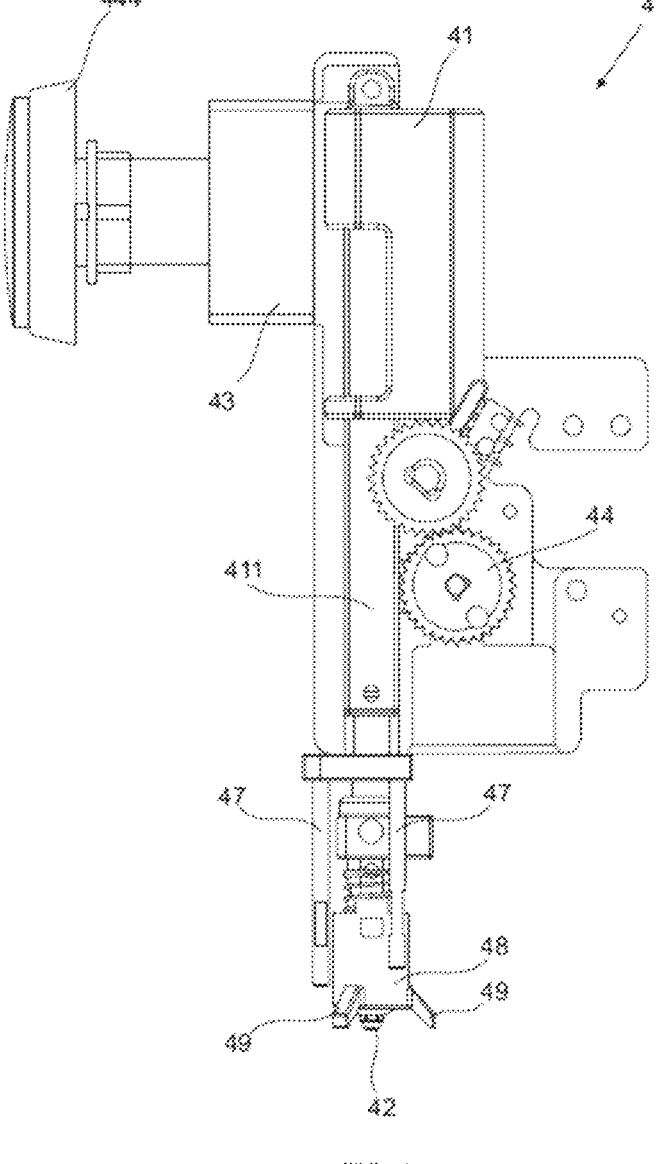
FIG. 15 depicts the glove-lifting-and-positioning device (4) when the movable rod (411) is in "up" position.
Figure 16:
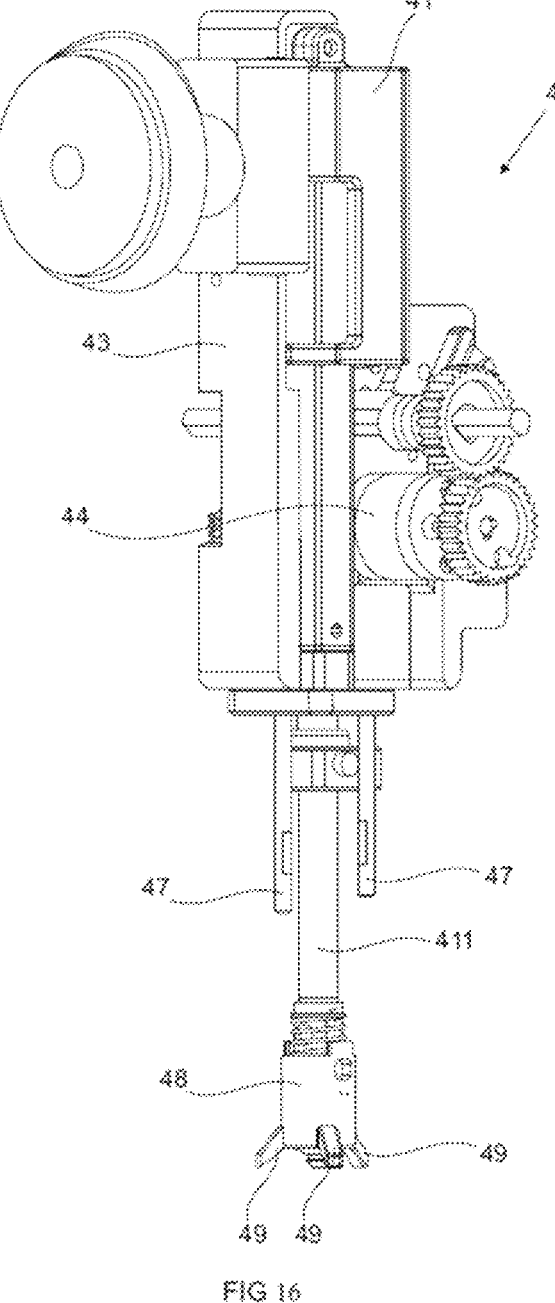
FIG. 16 depicts the glove-lifting-and-positioning device (4) when the movable rod (411) is in "down" position.
Figure 17:
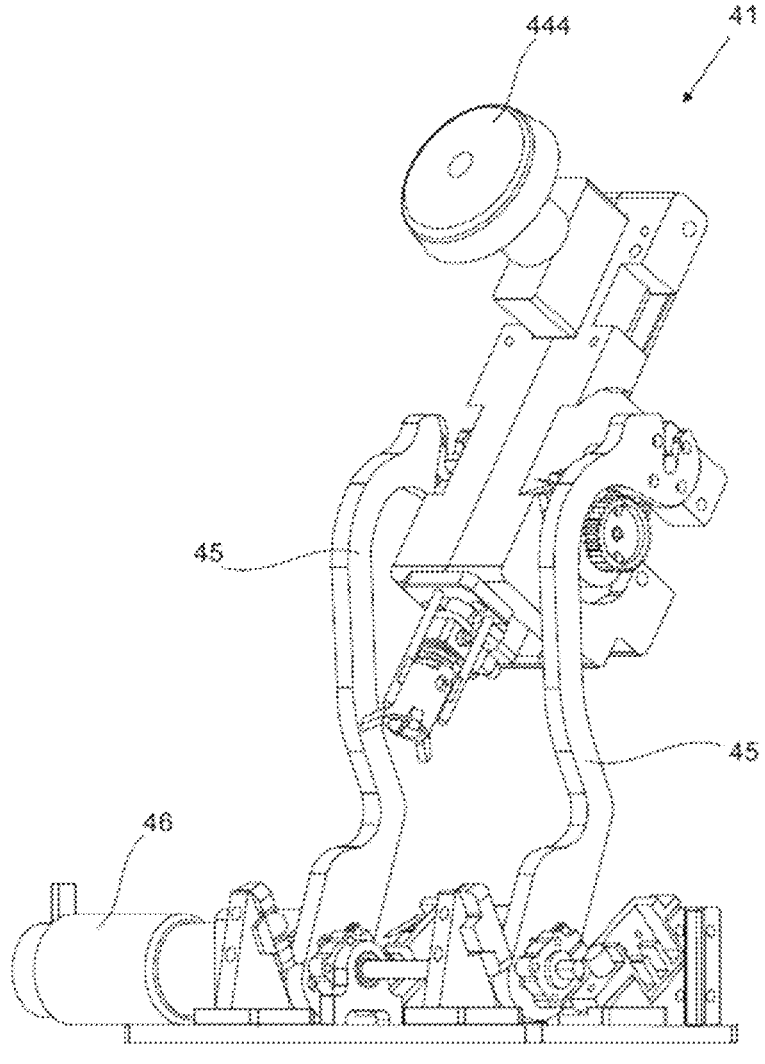
FIGS. 17 and 18 depict the glove-lifting-and-positioning device (4) in diagonal position.
Figure 18:
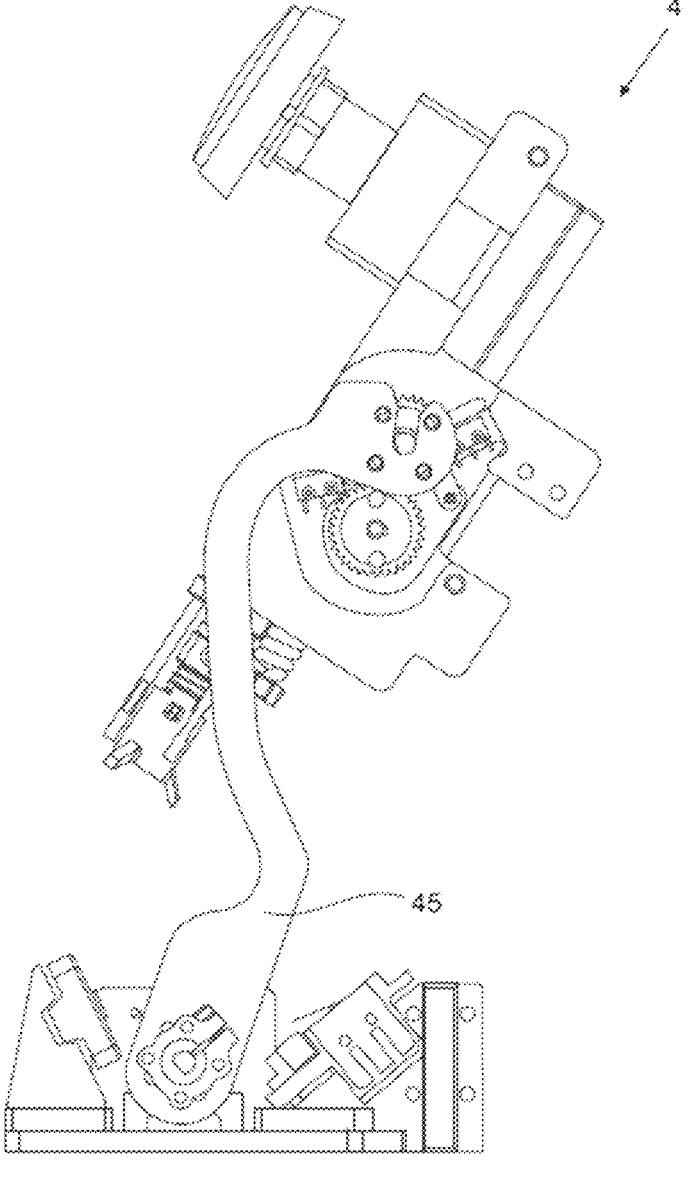
Figure 19:
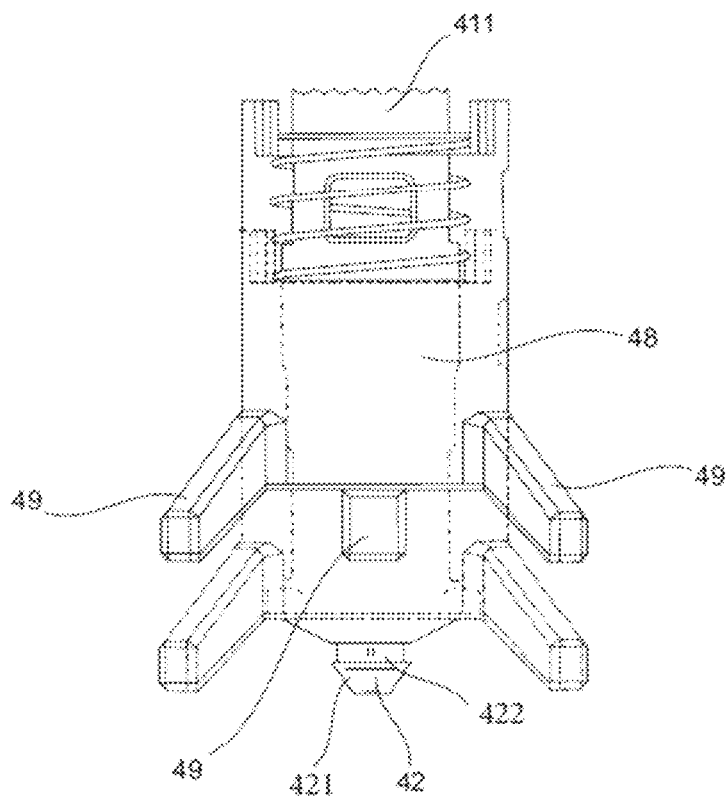
FIG. 19 depicts the adjustment piece (48) in two states relative to the movable rod (411).
Figure 20:
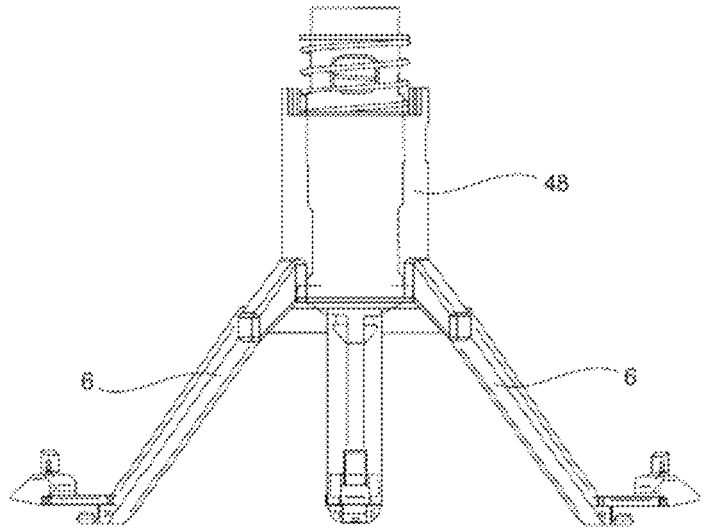
FIGS. 20 and 21 depict the inserting pin (42) when inserted in the glove holder.
Figure 21:
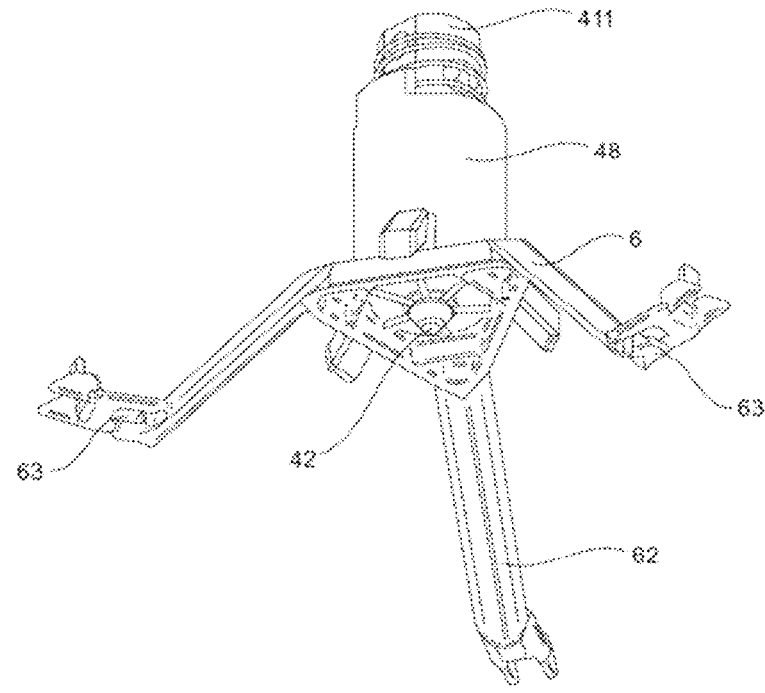
Figure 22:
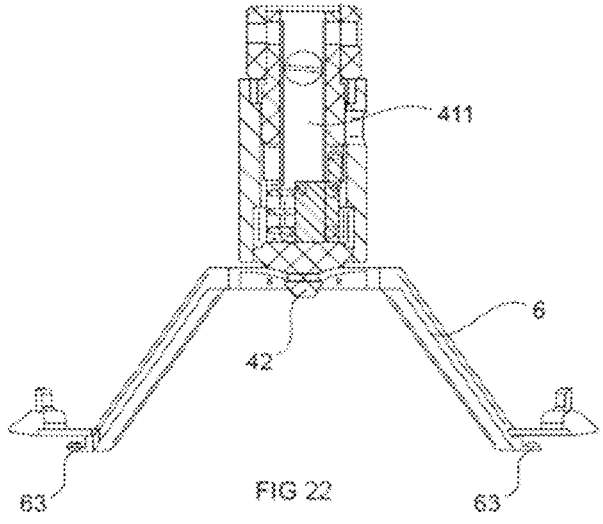
FIGS. 22 and 23 depict the inserting pin (42) before and after being inserted into the glove holder (6).
Figure 23:
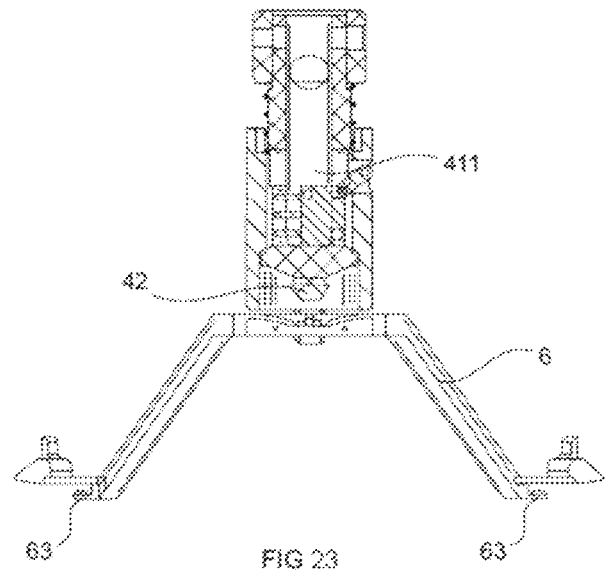
Figures 24A, 24B, 24C, 24D, 24E:
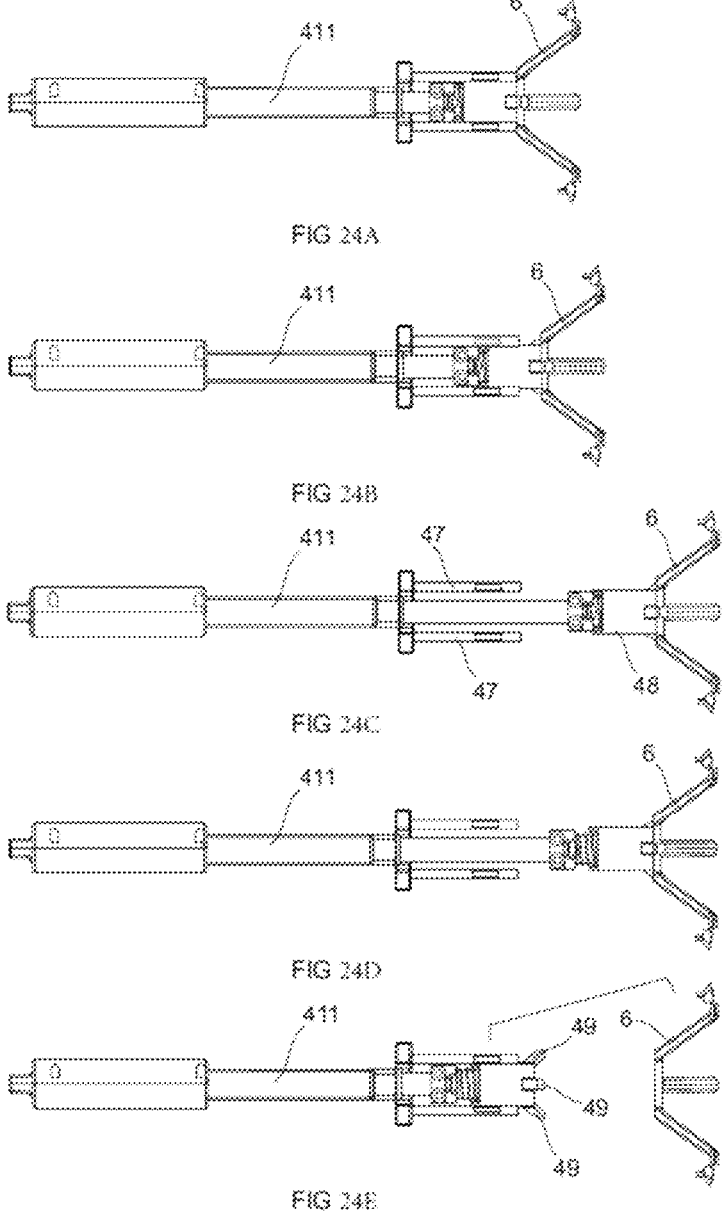
FIGS. 24A-24E depict several states of the movable rod (411) and the glove holder (6).
Figure 25:
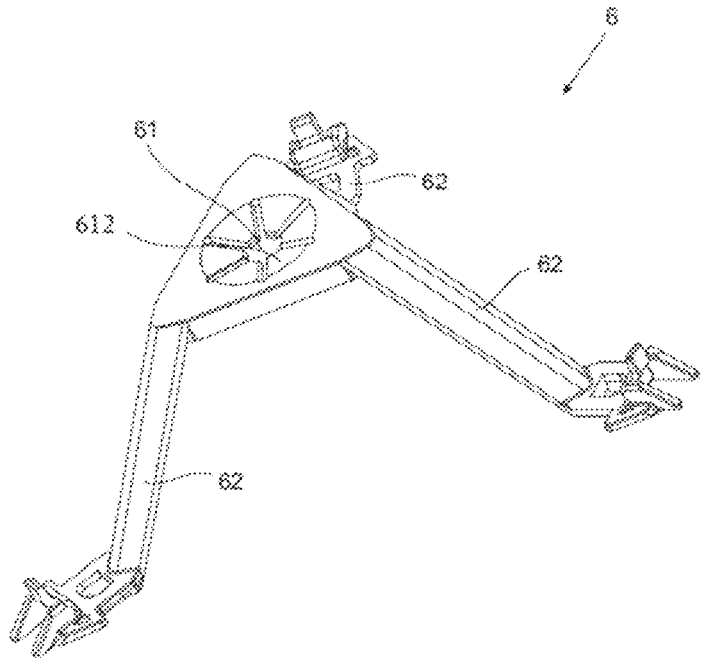
FIG. 25 depicts the glove holder (6).
Figure 26:
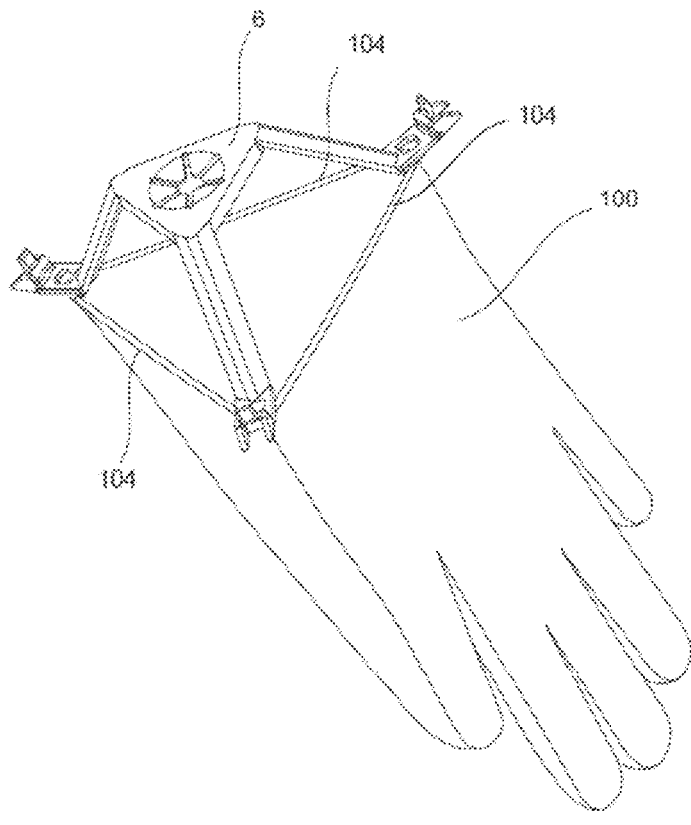
FIG. 26 depicts the glove holder (6) with a glove (100).

FIG. 14 depicts the glove (100) when inserted on the grasping pins and inflated and ready to receive the user's hand. FIG. 15 depicts the glove-lifting-and-positioning device (4) when the movable rod (411) is in "up" position and FIG. 16 depicts the glove-lifting-and-positioning device (4) when the movable rod (411) is in "down" position. FIGS. 17 and 18 depict the glove-lifting-and-positioning device (4) in diagonal position. FIG. 19 depicts the adjustment piece (48) in two states relative to the movable rod (411). FIGS. 20 and 21 depict the inserting pin (42) when being inserted into the glove holder (6). FIGS. 22 and 23 depict the inserting pin (42) before and after being inserted into the glove holder (6). FIGS. 24A-24E depict several states of the movable rod (411) and the glove holder (6). FIG. 25 depicts the glove holder (6). FIG. 26 depicts the glove holder (6) with a glove (100).

Figure 27:
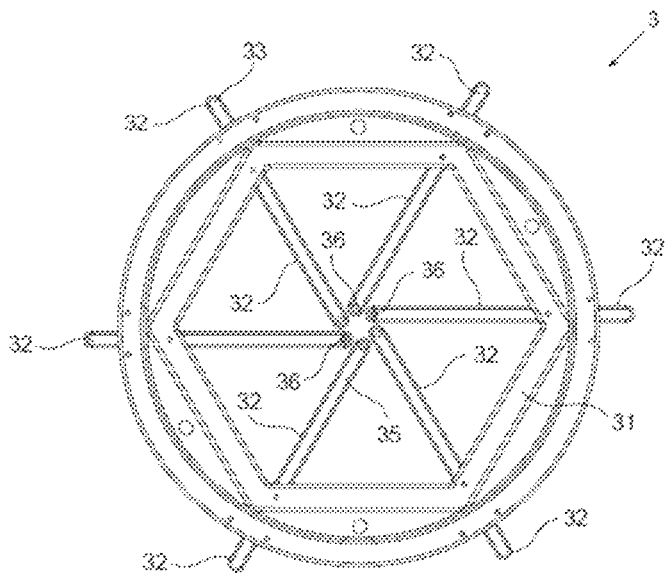
FIGS. 27 and 28 depict the glove-opening device (3) wherein the grasping pins (36) are concentrated in the center of the polygonal circumferential frame (31).
Figure 28:
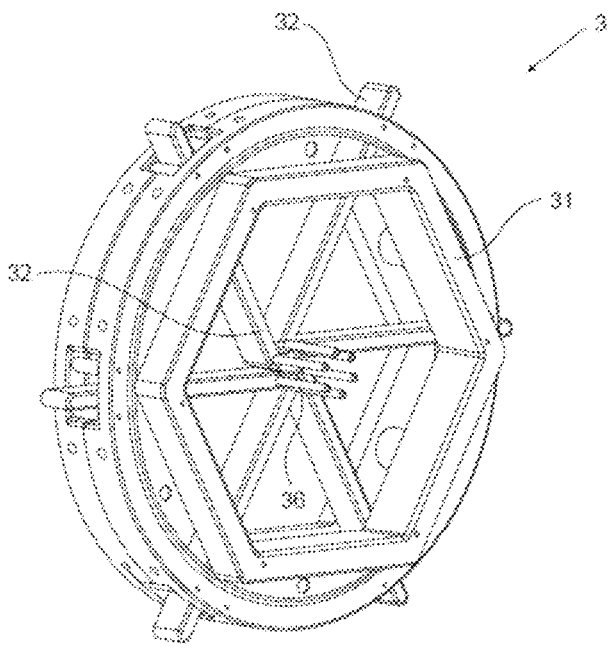
Figure 29:
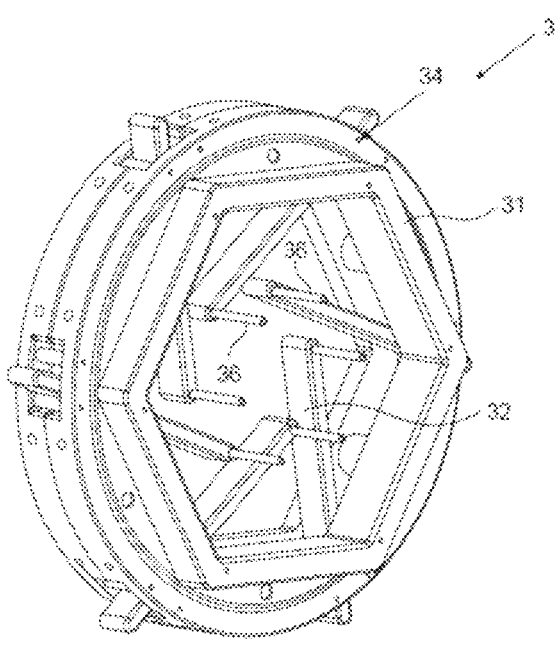
FIG. 29 depicts the glove-opening device (3) in partially opened position.
Figure 30:
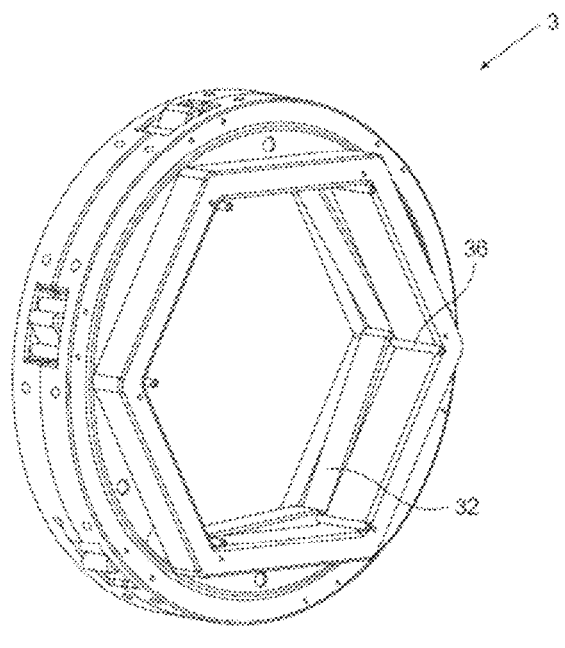
FIG. 30 depicts the glove-opening device (3) in an open position.
Figure 31:
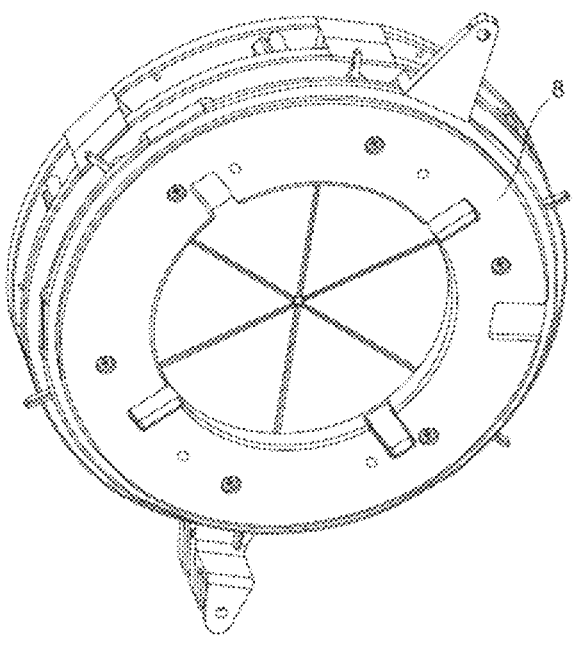
FIGS. 31-33 depict the adjuster (8) in several states.
Figure 32:
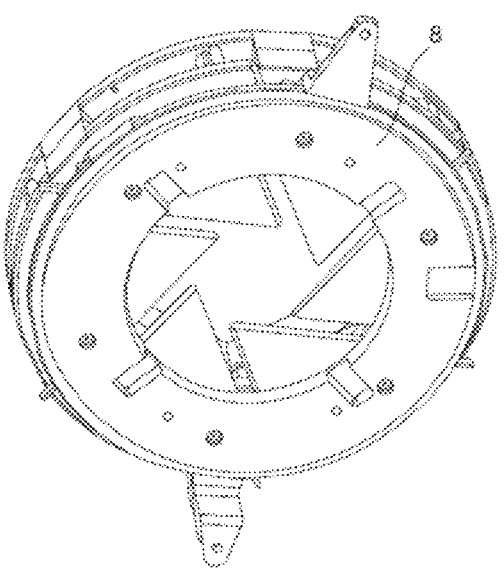
Figure 33:
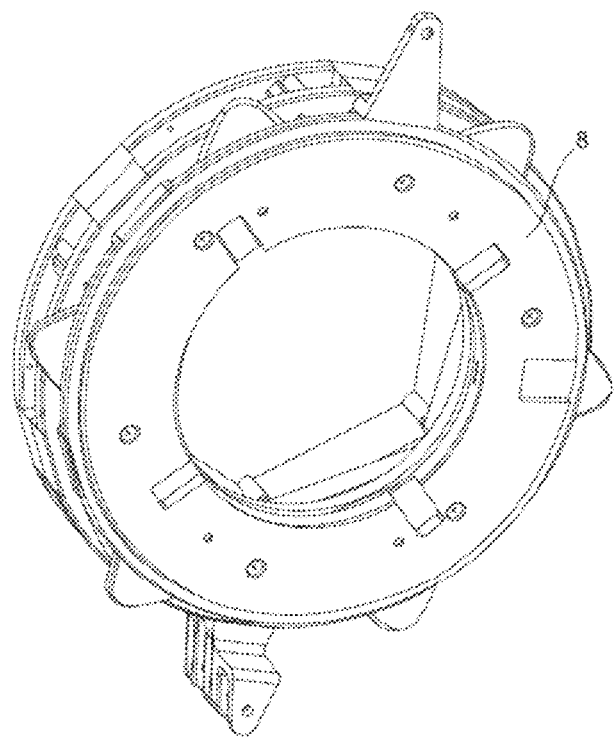

FIGS. 27 and 28 depict the glove-opening device (3) wherein the grasping pins (36) are concentrated in the center of the polygonal circumferential frame (31), i.e. in a closed position. FIG. 29 depicts the glove-opening device (3) in partially opened position, i.e. the spreading rods (32) are rotated slightly so that their inner ends (35) are closer to the sides of the polygonal circumferential frame (31). FIG. 30 depicts the glove-opening device (3) in an open position, i.e. when the spreading rods (32) are parallel and adjacent to the sides of the polygonal circumferential frame (31) and the grasping pins (36) are positioned in the angles between said sides of the polygonal circumferential frame. FIGS. 31-33 depict the adjuster (8) in several states.

The replaceable cartridge (7) and the glove holder (6) are described and explained above and in the drawings, and hereinafter we will describe them with more details. It is preferably that the gloving apparatus (1) will includes a replaceable cartridge (7) of gloves (100) and more preferably that the gloving apparatus will includes several replaceable cartridges (7).

Figure 34:
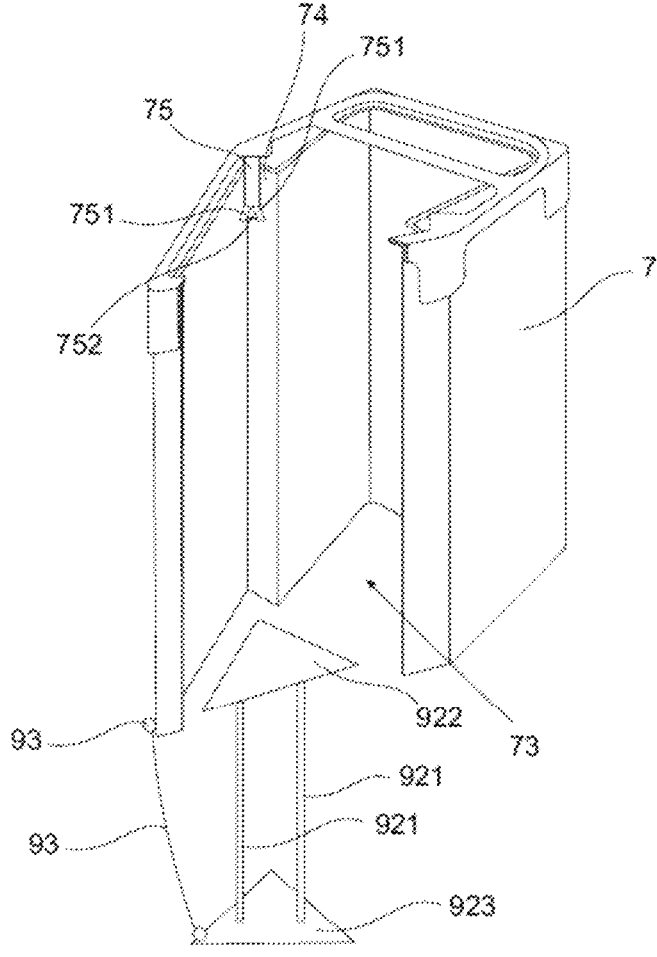
FIG. 34 is a partial cross section view of the replaceable cartridge (7) with the follower (92) and the spring (93).

The gloving apparatus (1) includes a cartridge mechanism (90) that includes a cartridge housing (91), a follower (92) and a spring (93). The follower (92) may include a pushing rod (921) that equipped with a pushing plate (922) in its upper end and with a pulling plate (923) in its bottom end, as depicted for example in FIG. 34. One end of the spring (93), preferably a type of constant-force spring, is attached to the bottom of the cartridge housing (91) and the other end of the spring is attached to the pulling plate (923), in such a way that the spring exerts pressure on the follower (92) to move upward through the cartridge housing and push up the holders (6) with the gloves (100), resembling the manner as a rifle cartridge/magazine works.

The cartridge mechanism (90) may include several cartridge housings (91) and with relevant parts such as the followers and the springs, and an activator that rotates the cartridge mechanism for aligning the relevant replaceable cartridge with the inserting pin (42). FIGS. 2 and 3 depict the gloving apparatus with the cartridge mechanism (90) that contains several replaceable cartridges (7).

The user can insert into each cartridge housing (91) a replaceable cartridge (7) through the upper opening of the cartridge housing and by that to push and press down the follower (92), and then to lock the replaceable cartridge to the housing. The spring (93) which is now in a tense state activates upward power on the follower (92) as explained above. Whenever a glove holder (6) is pulled out of the cartridge (7), the follower (92) raises slightly upward, the same as a rifle cartridge operation principle. When that replaceable cartridge is run out then the cartridge mechanism rotates a bit and aligns another cartridge to the inserting pin and when all the cartridges run out the user can replace them all.

The replaceable glove cartridge (7) is designed to contain several glove holders (6), one on top of the other, while a glove (100) is attached to each one of them. The replaceable cartridge (7) comprises a closed peripheral wall (71) with an upper opening (72) through which the glove holders (6) can be pulled out from the replaceable cartridge and a lower opening (73) through which the follower (92) can penetrate and push upwards the glove holders (6).

The replaceable cartridge (7) includes at least three inner corners (74) that serve as a guide for the glove holders (6) when they are inside the cartridge. In this way, the gloves holders (6) are positioned inside the cartridge in a way that the end of each holding rod (62) is positioned in each inner corner (74), so, when the glove holder includes three legs, means three holding rods then the cartridge should include at least three inner corners, and so forth.

Figure 35:
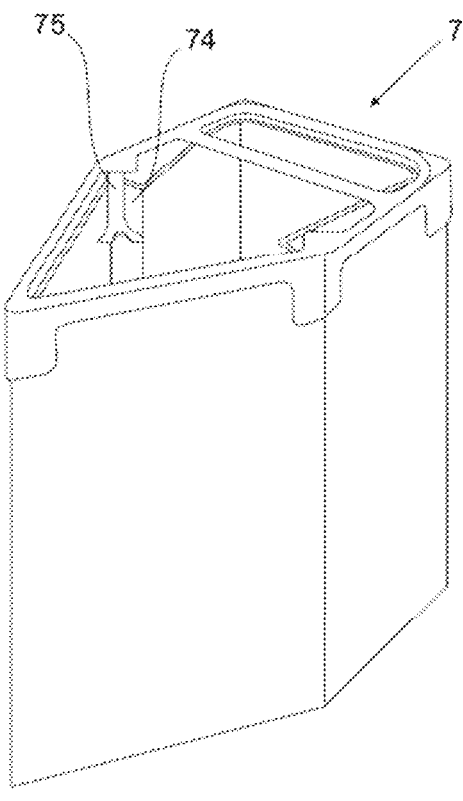
FIG. 35 depicts an empty replaceable cartridge (7).
Figure 36:
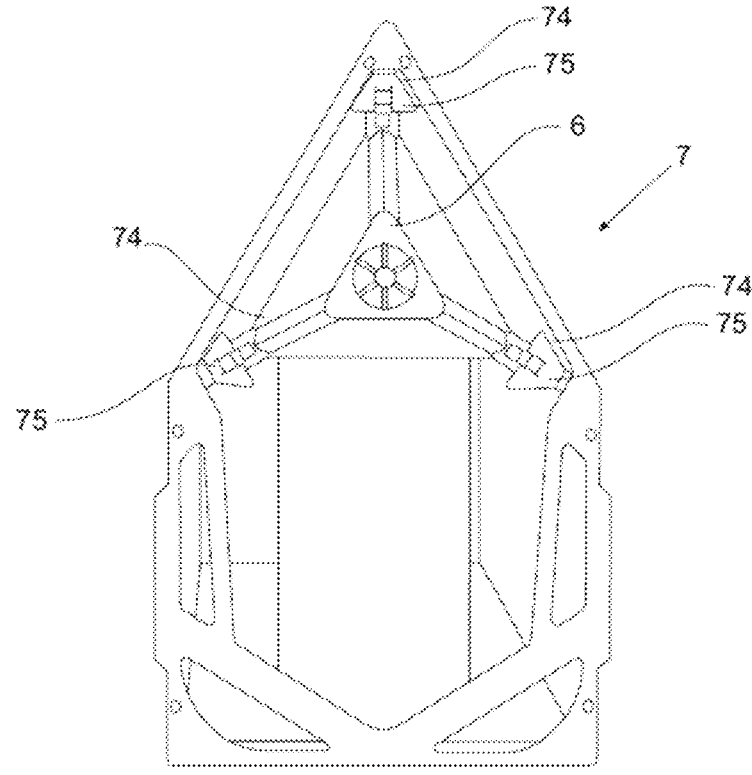
FIG. 36 is a top view of the replaceable cartridge (7).
Figure 37:
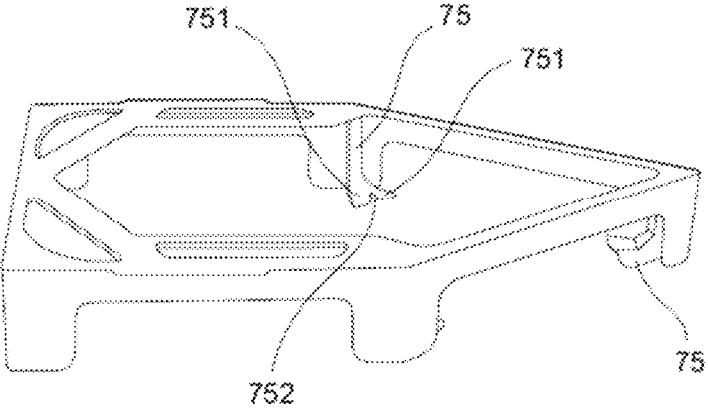
FIG. 37 is a top frame of the cartridge that includes the stoppers (75).

Along two or more of the inner corners (74), or all of them, there is a stopper (75) that is deigned to stop the upward movement of the glove holders (6). The stoppers (75) may be corresponds with the end (64) of the holding rod (62). For example, the stopper (75) may comprises two horizontal protrusions (751) with a gap (752) between them that correspond with the end (64) of the holding rod (62) that comprises two horizontal pieces (641) with a vertical piece (642) between them. In this way, the two horizontal protrusions (751) of the stopper (75) prevent the two horizontal pieces (641) from moving upward while the vertical piece (642) of the glove holder (6) is positioned inside the gap (752) and by that the upper glove holder (6) in the cartridge is located properly in the place to meet the inserting pin (42). The glove holder (6) may be made of a flexible material so that when the inserting pin (42) penetrates through the matching hole (61) of the glove holder (6), locks it and pulls it up, the holding rods (62) bend and the glove holder is able to be pulled out from the cartridge. FIG. 35 depicts an empty cartridge (7), FIG. 4 depicts it with glove holders (6), FIG. 36 is a top view of the cartridge (7) and FIG. 37 is a top frame of the cartridge that includes the stoppers (75).

As explained above and will explained hereinafter the glove holder (6) comprises a base (60) and at least three holding rods (62). The base (60) comprises a matching hole (61) with several horizontal slots (611) that match with the inserting pin (42). The inserting pin (42) comprises a rounded mushroom tip (421) and a polygonal stem (422). The rounded mushroom tip (421) enables the inserting pin (42) to easily penetrate through the matching hole (61) and to prevent it to be pulled out easily. It is possible to design the base in a way that the area (612) around the matching hole and between the will inclines towards the hole to allow easier penetration of the inserting pin and to prevent the pin to exit easily from the hole. The polygonal stem (422) is positions inside the matching hole (61) while surrounding by the ends of the horizontal slots (611) that prevents a rotary movement of the glove holder (6) around the inserting pin (42). The end (64) of each one of the at least three holding rods (62) comprises a holding clip (63) to which the circumferential part (104) of the opening (103) of the glove (100) is attached, and two horizontal pieces (641) with a vertical piece (642) between them. When the glove holders (6) are positioned inside the cartridge, one on top of the other, then the vertical piece (642) of each glove holder is situated between the two horizontal pieces (641) of the glove holder above it, and by that the glove holders are arranged in a stable and orderly manner one on top of the other inside the cartridge.

The objective of the present invention is to provide improvements to the gloving apparatus (1) of PCT/IL2020/051334 and as explained in details above mainly by using a plurality of inserting teeth (450) instead of the inserting pin (42) and using a plurality of matching holes (610) instead of the matching hole (61), all as explained hereinafter and as depicted in FIGS. 38-44.

In the improvements, the movable rod (411) is ended with the plurality of inserting teeth (450), wherein each inserting teeth (450) includes a horizontal arm (451) and a vertical arm (452) that ends with a slope (453) the form a horizontal step (454). Each of said plurality of teeth (450) is connected to the moving arm (411) by an axial connection (455) and by a spring (456), in such a way that when the tooth (450) moves toward the glove holder (6) the slope (453) meets the corresponding matching hole (610) in the glove holder (6) and causes the tooth to rotate on said axial connection against the force of the spring and by that enabling the penetration of the tooth into the corresponding matching hole out of said plurality of matching holes, and the spring is designed to cause the tooth to rotate back to a position in which the horizontal step firmly holds the bottom part (613) of the area (612) of the matching holes (610) as illustrated for example in FIGS. 49A and 49B. The releasing of the glove holder from the matching teeth is done by the releasing rods (47) that press on the horizontal arm (451) of the tooth (450) and by that releasing the horizontal step (454) from the bottom part (613) of the glove holder (6) and by that enabling the tooth to be pulled out from the matching hole.

Figure 38:
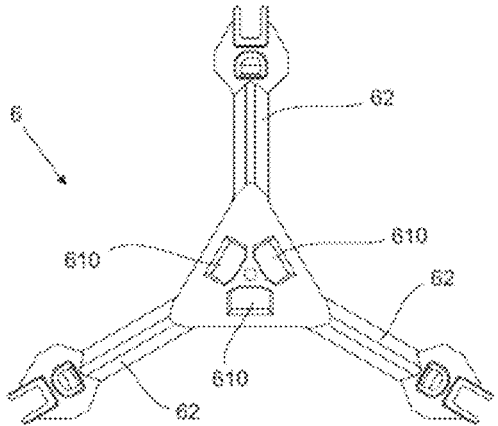
FIG. 38 depicts the glove holder (6) with the plurality of matching holes (610).
Figure 39:
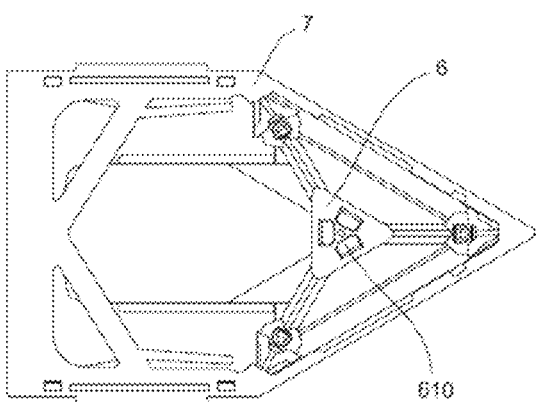
FIG. 39 depicts the cartridge (7) with plurality of glove holders (6).
Figures 40, 41, 42, 43:
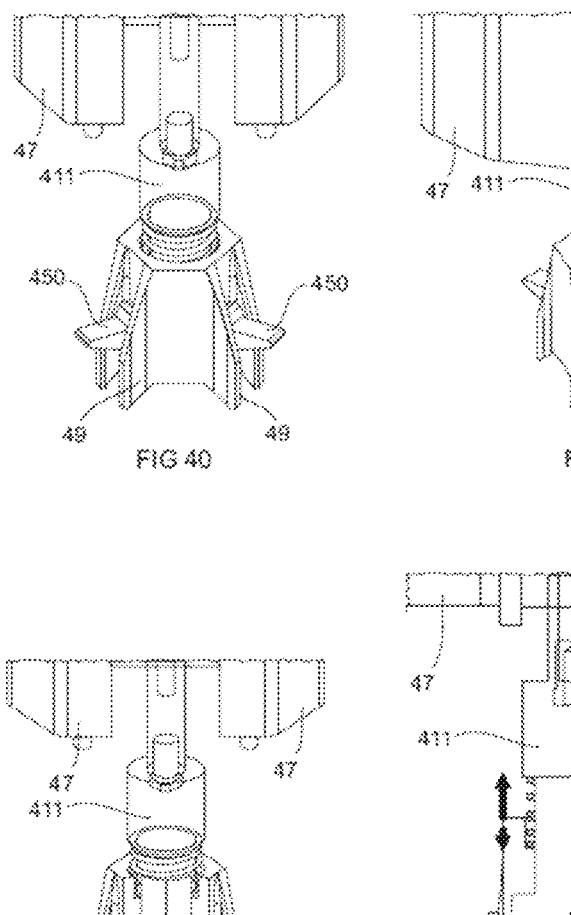
FIGS. 40-44 depict the end of the moving rod (411) and the plurality of the inserting teeth (450).
Figures 44, 45, 46, 47:
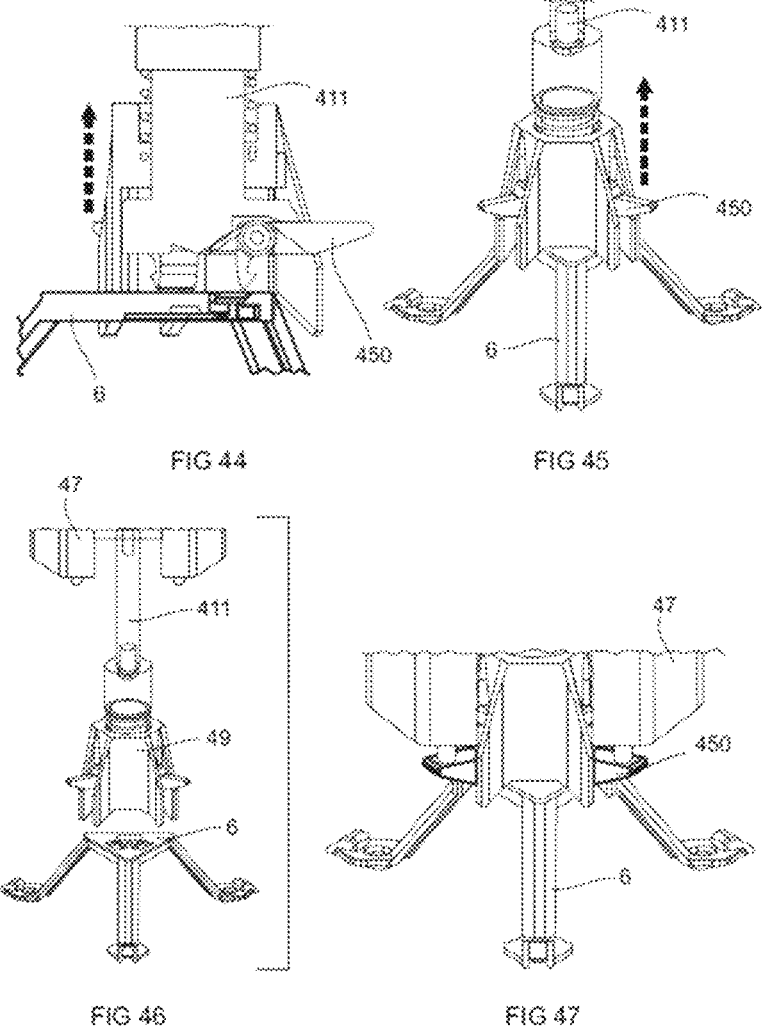
FIGS. 45-48 depict the end of the moving rod (411) and the plurality of the inserting teeth (450) together with a glove holder (6).
Figure 48:
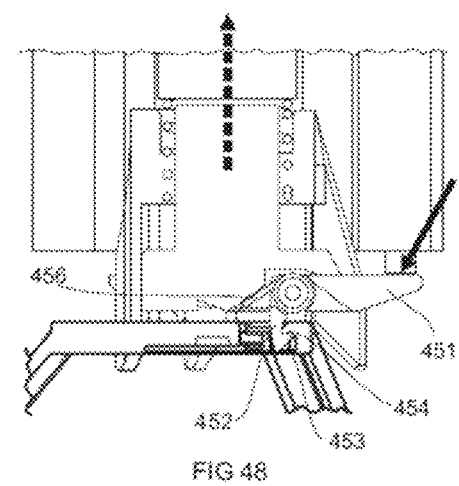
Figure 49A:
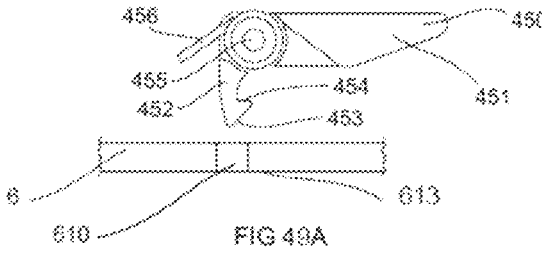
FIGS. 49A and 49B illustrate the horizontal step (454) in relation to the glove holder (6).
Figure 49B:
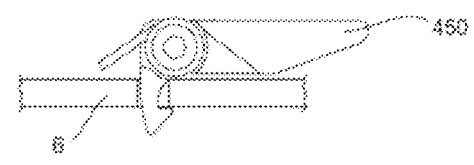

The use of the plurality of inserting teeth (450) and the corresponding plurality of matching holes (610) enables the moving rod to grasp the glove holder in a stable manner without the glove holder moving in different directions, but rather being in a fixed position relative to the moving rod, thus allowing the glove holder to be moved with the glove firmly to the appropriate place. FIG. 38 depicts the glove holder (6) with the plurality of matching holes (610), FIG. 39 depicts the cartridge (7) with plurality of glove holders (6) (visible only the top one), FIGS. 40-44 depict the end of the moving rod (411) and the plurality of the inserting teeth (450), FIGS. 45-48 depict the end of the moving rod (411) and the plurality of the inserting teeth (450) together with a glove holder (6), and FIGS. 49A and 49B illustrate the horizontal step (454) in relation to the glove holder (6). The gloving apparatus is designed to include at least one replaceable cartridge with glove holders and gloves.

What is claimed is:

1. A gloving apparatus that comprises a casing, a glove-opening device, a glove-lifting-and-positioning device, and an air pump;

wherein the glove-lifting-and-positioning device includes a base with a linear actuator that is equipped with a movable rod, a rotating actuator that is designed to rotate the glove-lifting-and-positioning device, and a lifting arm with a lifting actuator, wherein the lifting arm is designed to lift up and lower down the glove-lifting-and-positioning device;

wherein said base includes releasing rods; wherein said movable rod is ended with a plurality of inserting teeth;

wherein the glove-opening device comprises a polygonal circumferential frame and several spreading rods; wherein an outer end of each spreading rod is attached to the polygonal circumferential frame via an axial joint; and wherein an inner end of each spreading rod is equipped with a grasping pin;

wherein the glove-lifting-and-positioning device is designed to move up and down and back and forth and to insert the plurality of inserting teeth of the movable rod into a plurality of corresponding matching holes at a glove holder to which a glove is attached and to lift the glove holder with the glove and insert an opening of the glove over said grasping pins;

wherein the glove-opening device is designed to move from a closed position to an open position, causing the glove opening to stretch open and assume the shape of the polygonal circumferential frame; wherein the air pump is designed to create sub-pressure in the casing, causing the glove to expand to a size and shape suitable for a hand to be inserted into the expanded glove.

2. The gloving apparatus of claim 1 wherein each of said plurality of inserting teeth includes a horizontal arm and a vertical arm with a slope that forms a horizontal step, and wherein each of said plurality of inserting teeth is connected to the movable rod by an axial connection and by a spring.

3. The gloving apparatus of claim 1 that further includes at least one replaceable glove cartridge that contains glove holders with gloves; wherein the at least one replaceable glove cartridge comprises a closed peripheral wall and at least two stoppers;

wherein said closed peripheral wall includes at least three inner corners that are designed to serve as a guide for the glove holders, an upper opening through which the glove holders are designed to be pulled out, and a lower opening through which a follower is designed to to penetrate and push upwards the glove holders;

wherein the stoppers are situated along at least two of the at least three inner corners and wherein said stoppers are designed to stop an upward movement of the glove holders when they are pushed upwardly only by the follower;

wherein each of said stoppers corresponds with an end of a holding rod of each one of said glove holders; wherein each stopper comprises two horizontal protrusions with a gap between them, wherein the two horizontal protrusions with the gap correspond with the end of the holding rod of the each one of said glove holders that comprises two horizontal pieces with a vertical piece between them.

\* \* \* \* \*